(12) United States Patent
Kim et al.

(10) Patent No.: US 12,070,290 B2
(45) Date of Patent: Aug. 27, 2024

(54) GUIDEWIRE COUPLED HELICAL MICROROBOT SYSTEM FOR MECHANICAL THROMBECTOMY

(71) Applicant: INDUSTRY FOUNDATION OF CHONNAM NATIONAL UNIVERSITY, Gwangju (KR)

(72) Inventors: Chang Sei Kim, Gwangju (KR); Jong Oh Park, Gyeonggi-do (KR); Eun Pyo Choi, Gwangju (KR); Byung Jeon Kang, Gwangju (KR); Kim Tien Nguyen, Gwangju (KR); Gwang Jun Go, Gwangju (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 860 days.

(21) Appl. No.: 17/059,597

(22) PCT Filed: Mar. 21, 2019

(86) PCT No.: PCT/KR2019/003320
§ 371 (c)(1),
(2) Date: Nov. 30, 2020

(87) PCT Pub. No.: WO2019/231088
PCT Pub. Date: Dec. 5, 2019

(65) Prior Publication Data
US 2021/0220068 A1    Jul. 22, 2021

(30) Foreign Application Priority Data

May 28, 2018 (KR) ................ 10-2018-0060669

(51) Int. Cl.
*A61B 34/00* (2016.01)
*A61B 17/00* (2006.01)
(Continued)

(52) U.S. Cl.
CPC ........ *A61B 34/73* (2016.02); *A61B 17/00234* (2013.01); *A61B 17/320758* (2013.01);
(Continued)

(58) Field of Classification Search
CPC .......... A61B 17/320758; A61B 2017/320004; A61B 2017/320766; A61B 17/320725;
(Continued)

(56) References Cited

U.S. PATENT DOCUMENTS 6,156,046 A * 12/2000 Passafaro ............. A61B 17/221
606/159
2016/0235491 A1* 8/2016 Choi ..................... A61B 34/30
(Continued)

FOREIGN PATENT DOCUMENTS

CN    103064049 A  *  4/2013
CN    107984306 A  *  5/2018  ............. B24B 1/005
(Continued)

OTHER PUBLICATIONS

Yu, Chang-ho et al., "Multifunctional Robotic Guidewire System using Spiral-type Magnetic Micro robot witll Magnetic Manipulation. In: Journal of Magnetics", The Korean Magnetics Society. vol. 2]. Issue 4, 6 (6-621, ISSN (Online) 2233-6656, Dec. 31, 2016. (Year: 2016).*
(Continued)

*Primary Examiner* — Katherine M Shi
(74) *Attorney, Agent, or Firm* — Harness, Dickey & Pierce, P.L.C.

(57) ABSTRACT

The present invention relates to a medical robot system capable of effectively removing a calcified thrombus in a blood vessel. The present invention proposes a new guide-wired helical microrobot for mechanical thrombectomy applied to a calcified thrombus. Also, the present invention proposes an electromagnetic navigation system (ENS)
(Continued)

which uses a high frequency operation that is based on a resonant effect in order to enhance the boring force of a microrobot. The microrobot system of the present invention can precisely tunnel through a blood vessel blockage site by means of the electromagnetic navigation system without damaging blood vessel walls. The microrobot system of the present invention has a wide range of applications including not only for thrombosis, but also thromboangiitis obliterans caused by vasoocclusion, cerebral infarction, strokes, angina or myocardial infarction, peripheral artery occlusive disease, or atherosclerosis, etc.

8 Claims, 11 Drawing Sheets

(51) Int. Cl.
*A61B 17/3207* (2006.01)
*A61B 34/20* (2016.01)
*A61B 34/30* (2016.01)
*A61B 90/00* (2016.01)
*A61M 25/09* (2006.01)

(52) U.S. Cl.
CPC .............. *A61B 34/20* (2016.02); *A61B 34/30* (2016.02); *A61B 2017/00345* (2013.01); *A61B 2034/303* (2016.02); *A61B 2034/732* (2016.02); *A61B 2090/3762* (2016.02); *A61B 2090/378* (2016.02); *A61M 2025/09183* (2013.01)

(58) Field of Classification Search
CPC ...... A61B 2017/22038; A61B 17/3207; A61B 2017/00685; A61B 2017/003; A61B 17/320016; A61B 17/32002; A61B 2017/320024; A61B 2017/320028; A61B 2017/320032; A61B 17/221; A61B 2017/22039; A61B 2017/22042; A61B 2017/22044; A61B 2017/22081; A61B 2017/22094; A61B 2017/22095; A61B 2017/320775; A61B 34/72; A61B 34/73; A61B 2034/731; A61B 34/70; A61B 34/30; A61B 2034/303; A61B 90/37; A61B 2090/376; A61B 2090/3762; A61B 2017/00345; A61B 2034/2051; A61B 5/062; A61B 34/00; A61B 34/10; A61B 34/20; A61B 2034/2046; A61B 2034/301; A61B 5/0031; A61B 1/00158; A61B 17/00234; A61B 2218/007; A61B 2017/00411; A61B 2090/378

See application file for complete search history.

(56) References Cited

U.S. PATENT DOCUMENTS

2018/0280045 A1\* 10/2018 Malhi ................ A61B 18/1492
2019/0388109 A1\* 12/2019 Cai .................. A61B 17/22004

FOREIGN PATENT DOCUMENTS

| CN | 208637138 U | \* | 3/2019 | |
|---|---|---|---|---|
| KR | 10-0972253 B1 | | 7/2010 | |
| KR | 20100136206 A | \* | 12/2010 | |
| KR | 20110033573 A | \* | 3/2011 | |
| KR | 10-2011-0127339 A | | 11/2011 | |
| KR | 20110127339 A | \* | 11/2011 | |
| KR | 10-1487337 B1 | | 1/2015 | |
| KR | 10-1765015 B1 | | 8/2017 | |
| WO | WO-2013032792 A1 | \* | 3/2013 | ............ A61M 25/10 |

OTHER PUBLICATIONS

International Search Report from corresponding PCT Application No. PCT/KR2019/003320, dated Jul. 11, 2019.
Nam, Jaekwang et al. "Magnetic Navigation System Utilizing Resonant Effect to Enhance Magnetic Field Applied to Magnetic Robots. In: IEEE Transactions on Industrial Electromcs". vol. 64, Issue 6, pp. 4701-4709, Feb. 15, 2017.
Kim. Tien et al. Powerful, High-frequency Electromagnetic Actuation System for Cardiovascular Therapeutic Applicmions. In: 2018 Proceedings of Spring Conference. Korean Society of Percision Engineering. | 8SPP469. Ramada Plaza Jeju Hotel), May 11, 2018.
Filipp, S., "New aspects of the quantum geometric phase", INIS vol. 38, INIS Issue 16, 2006.

\* cited by examiner

GUIDEWIRE COUPLED HELICAL MICROROBOT SYSTEM FOR MECHANICAL THROMBECTOMY

CROSS-REFERENCE TO RELATED APPLICATIONS

This application is a national phase application of PCT Application No. PCT/KR2019/003320, filed on Mar. 21, 2019, which claims the benefit and priority to Korean Patent Application No. 10-2018-0060669, filed on May 28, 2018. The entire disclosures of the applications identified in this paragraph are incorporated herein by references.

FIELD

The present invention relates to a guide-wired microrobot system for mechanical thrombectomy. More specifically, the present invention relates to a medical robot system composed of a helical microrobot equipped with a guidewire at the tip thereof, an electromagnetic actuation system for rapidly rotating the helical microrobot, and a real-time imaging system.

The present invention was made with the support of the Ministry of Science and ICT in Korea under Project No. 2015M3D5A1065682, which was carried out in the program entitled "Development of External-Controlled Capsule and Multi-functional Modules" in the project named "Development Work of New Market Creating Next-Generation Medical Devices" by the Industry Foundation of Chonnam National University under management of the National Research Foundation of Korea, from 1 Nov. 2015 to 31 Oct. 2018.

BACKGROUND

Mechanical thrombectomy has been proposed as one alternative to intravascular therapeutics using tissue plasminogen activator (tPA). The therapeutics using the tissue plasminogen activator have restrictive time window after stroke onset and are less effective in large vessel treatment. As a result of using advanced catheterization technology, such as Merci retriever with corkscrew distal wires or balloon catheterization, Solitaire stent retriever, and direct aspiration in mechanical thrombectomy, the recanalization rate has become higher and faster than before.

However, during utilization of such devices, very skillful operators are required for the improvement of patient conditions. In addition, the operators have to directly operate the devices under X-ray monitoring devices, resulting in a risk associated with the operator's exposure to radiation.

In order to overcome those problems and accomplish remote operations, a magnetically steering guidewire controlled by an electromagnetic navigation system (ENS) has been developed.

The magnetically steering guidewire has been considered as a promising approach due to its advantages of wireless actuation, multi-degree of freedom controllability, strong actuation force, modifiable size and shape, and low cost.

A lot of research has been conducted in order to effectively control a guidewire equipped with a small permanent magnet in the tip thereof by using ENS For example, the forward and backward motion of the guidewire by a motorized feeding device was attempted to break a thrombus, but this method was not effective in passing through the thrombus due to low stiffness of the guidewire.

Therefore, a magnetic helical microrobot capable of drilling and locomotion was suggested by converting the applied electromagnetic torque into propulsion force through the use of a rotating magnetic field of the externally applied ENS. This magnetic helical microrobot is more advantageous in the removal of a thrombus in the blood vessel.

But, as a result of in-vivo experiments, it was very difficult to provide sufficient propulsion force and drilling force so that the helical microrobot moves into a target region and operates stably during a drilling procedure in the fast blood flow.

Meanwhile, the electromagnetic navigation system (ENS) requires a high-frequency alternating electromagnetic field for stable locomotion and strong drilling force of the helical microrobot.

However, in the conventional ENS, the high-frequency of an input voltage strongly affected the coil impedance and phase delay to cause a deterioration in magnetic force and controllability. In some cases, the input voltage required for the system exceeded the available maximum power to cause excessive power consumption. Meanwhile, a series of capacitors connected to the coils, which can compensate for a frequency of up to 75 Hz without phase delay, has been proposed, but this has a limitation of manual frequency switching in a specific range.

According to most of previous studies, the maximum current was restricted by the capacity of the output current of an amplifier driver, thereby preventing the use of a high electromagnetic field. Eventually, for the successful implementation of the intravascular microrobot for mechanical thrombectomy, a strong electromagnetic field and a stable microrobot motion against the blood flow are required.

Therefore, the present invention is intended to suggest feasible solutions to the problems related to an existing ENS and provide a mechanism of mechanical thrombectomy device applying the same.

SUMMARY

Technical Problem

The present inventors conducted research efforts to develop a microrobot capable of achieving stable operation and actuation against a strong electromagnetic field and the blood current in mechanical thrombectomy using a robot.

As a result, the present inventors developed a prototype of a helical microrobot equipped with a freely rotatable spherical joint.

The present inventors implemented an improved electromagnetic navigation system (ENS), which uses a high-frequency operation based on a resonant effect, in order to enhance the drilling force of the microrobot.

A microrobot system of the present invention is a medical robot system utilizing the helical microrobot and the electromagnetic navigation system.

The present inventors verified through in-vitro experiments that the electromagnetic navigation system successfully enhanced the locomotive force and drilling force of the microrobot, and thus completed the present invention.

Therefore, an aspect of the present invention is to provide an electromagnetic actuation system.

Another aspect of the present invention is to provide a method for controlling a microrobot by an electromagnetic actuation system.

Still another aspect of the present invention is to provide a medical microrobot system for use in the removal of calcified thrombi.

Technical Solution

In accordance with an aspect of the present invention, there is provided an electromagnetic actuation system including:
(a) 3-axis Helmholtz coils including one pair of circular Helmholtz coils disposed in an x-axial space, one pair of square Helmholtz coils disposed in a y-axial space, and one pair of square Helmholtz coils disposed in a z-axial space; and
(b) a variable capacitor connected in series to each of the Helmholtz coils.

The present inventors conducted research efforts to develop a microrobot capable of achieving stable operation and actuation against a strong electromagnetic field and the blood current and an electromagnetic actuation system therefor, in mechanical thrombectomy using a robot.

As a result, the present inventors developed a prototype of a helical microrobot equipped with a freely rotatable spherical joint. A guidewire for external control is connected to the spherical joint.

The helical microrobot of the present invention can remove calcified substances through a drilling procedure in the blood vessel. The guidewire helps supporting and operating the microrobot in the blood current during the removal of a thrombus.

The present inventors invented an electromagnetic navigation system, which uses a high-frequency operation based on a resonant effect, in order to enhance the drilling force of the microrobot.

Hereinafter, the electromagnetic actuation system, which is used in the control of the helical microrobot of the present invention, will be described in detail.

I. Electromagnetic Actuation System

The electromagnetic actuation system of the present invention includes 3-axis Helmholtz coils and variable capacitors.

The 3-axis Helmholtz coils include one pair of circular Helmholtz coils disposed in an x-axial space, one pair of square Helmholtz coils disposed in a y-axial space, and one pair of square Helmholtz coils disposed in a z-axial space. According to an embodiment of the present invention, the Helmholtz coils are square Helmholtz coils.

The electromagnetic actuation system may be designed such that two pairs of square Helmholtz coils are placed inside the circular Helmholtz coils to maximize the region of interest (ROI).

According to an embodiment of the present invention, in the 3-axis Helmholtz coils, one pair of square Helmholtz coils may be placed inside one pair of circular Helmholtz coils and another pair of Helmholtz coils may be positioned inside the pair of square Helmholtz coils (see FIG. 4B). The variable capacitors are connected in series to the Helmholtz coils, respectively.

As used herein, the term "electromagnetic actuation (EMA) system" may refer to a system that controls the three-dimensional locomotion and direction of a microrobot. The electromagnetic actuation system of the present invention includes a resonance control circuit, and can generate a wide range of resonant frequency with a maximum magnetic field and little phase delay.

The electromagnetic actuation system of the present invention can maximize the magnetic field generation frequency by using the resonance control circuit. That is, the uniform magnetic field generated in the Helmholtz coils is rapidly rotated (utilizing the high frequency of coils) around the locomotion planning path of the microrobot as the central axis, and the motion of the microrobot can be controlled using the propulsion force generated by the rotation of the microrobot.

According to an embodiment of the present invention, the resonant frequency range of the circular Helmholtz coils may be 15-100 Hz, the resonant frequency range of the square Helmholtz coils disposed in the y-axis space may be 25-135 Hz, and the resonant frequency range of the square Helmholtz coils disposed in the z-axis space may be 40-370 Hz.

FIG. 5 shows a wide operating frequency range of the electromagnetic actuation system of the present invention. As shown in FIG. 5, the controllable lowest to highest resonant frequencies of CHCx, SHCy, and SHCz are 16.58-100 Hz, 26.27-131.2 Hz, and 41.42-370 Hz, respectively. The operating frequencies of ENS can be controlled by an operator depending on the degree of blood vessel calcification, and thus can change the cutting rotation torque.

The Helmholtz coils can generate a uniform magnet field enabling the rotation and propulsion of a helical microrobot. According to an embodiment of the present invention, the Helmholtz coils of the present invention are one pair of circular Helmholtz coils disposed in the x-axis, y-axis, or z-axis space, and the uniform magnetic field generated from the Helmholtz coils of the present invention can be rapidly rotated (utilizing the high frequency of coils) to produce propulsion force of the microrobot.

The Helmholtz coils generates a uniform magnetic field, which produces the torque to align the microrobot in the three-dimensional space to thereby align the microrobot in any direction and changes the alignment direction of the microrobot so as to enable the rotation motion of the microrobot. Meanwhile, the propulsion force generated by the rotation of the microrobot is used to move the microrobot.

According to another embodiment of the present invention, the 3-axis Helmholtz coils of the present invention can generate a constant magnetic flux by magnetized currents, and can generate a magnetic field in any direction on three dimensions by adjusting the intensity and direction of the magnetized current of each coil.

The electromagnetic actuation system of the present invention can cancel the reactance of the electromagnetic coil by a variable capacitor selectively activated at the resonant frequency (fr) and deliver the maximum current at the resonant frequency (fr). The impedance of the variable capacitor is adjusted to match the reactance of the electromagnetic coil at the resonant frequency, and the maximum current is delivered by a zero phase delay at the resonant frequency.

$$f_r = \frac{1}{2\pi\sqrt{LC_v}}$$

(L: coil inductance, Cv: variable capacitance)

The electromagnetic actuation system of the present invention may further include a switch that selectively activates a variable capacitor (see FIG. 4A).

The electromagnetic actuation system of the present invention may further include a current amplifier that supplies a current to each electromagnetic coil (FIG. 4A).

II. Microrobot Control Method

In accordance with another aspect of the present invention, there is provided a method for controlling a microrobot, the method including:
(a) placing a microrobot inside an electromagnetic actuation system;
(b) applying a current to the electromagnetic actuation system to generate an electromagnetic field by 3-axis Helmholtz coils; and
(c) controlling the microrobot by adjusting the intensity and direction of a current applied to a microrobot magnetized by the electromagnetic field or a microrobot containing a ferromagnetic substance.

Since the method for controlling a microrobot of the present invention uses the above-described electromagnetic actuation system of the present invention, descriptions of overlapping contents therebetween are omitted to avoid excessive complexity of the present specification.

Hereinafter, the method for controlling a microrobot of the present invention will be described in detail.

Step (a): Step of Placing Microrobot Inside Electromagnetic Actuation System

First, a microrobot is placed inside an electromagnetic actuation system.

According to an embodiment of the present invention, the microrobot may move into the electromagnetic actuation system by a guidewire feeder disposed outside the electromagnetic actuation system. The microrobot is connected to a guidewire, which is connected with the guidewire feeder (see FIG. 1).

According to another embodiment of the present invention, the microrobot can move into the electromagnetic actuation system by the guidewire feeder disposed outside the electromagnetic actuation system, and can be inserted into the body of a subject inside the electromagnetic actuation system. For example, the subject is a mammal including a human.

Step (b): Step of Applying Current to Electromagnetic Actuation System to Generate Electromagnetic Field Then, a current is applied to the electromagnetic actuation system to generate an electromagnetic field by 3-axis Helmholtz coils. When the current is applied to the electromagnetic actuation system, a uniform magnetic field is generated by the 3-axis Helmholtz coils. The uniform magnetic field produces the torque to align the microrobot in the three-dimensional space to thereby align the microrobot in any direction and changes the alignment direction of the microrobot so as to enable the rotational motion of the microrobot.

The magnetic field generation frequency can be maximized by a resonance control circuit, thereby enhancing the propulsion force of the microrobot. That is, the uniform magnetic field generated in the Helmholtz coils is rapidly rotated (utilizing the high frequency of coils) around the locomotion planning path of the microrobot as the central axis. The locomotion of the microrobot can be controlled using the propulsion force generated by the rotation of the microrobot.

Step (c): Step of Adjusting Intensity and Direction of Current Applied to Microrobot The microrobot may contain a paramagnetic substance or a ferromagnetic substance. The paramagnetic substance is a substance which is magnetized by an external magnetic field and is not magnetized by the removal of the external magnetic field, and the ferromagnetic substance is a substance which is magnetized even without an external magnetic field.

When the microrobot contains a paramagnetic substance, the magnetic substance inside the microrobot is magnetized by an electromagnetic field of the 3-axis Helmholtz coils. The microrobot can be controlled by adjusting the intensity and direction of the magnetization current of the magnetized microrobot.

When the microrobot contains a ferromagnetic substance (e.g., a permanent magnet), the microrobot can be controlled by adjusting the intensity and direction of an input current.

According to an embodiment of the present invention, the electromagnetic actuation system can be externally remotely controlled by a control system disposed in a separated space.

For example, the control system may encompass: a monitor for observing the microrobot in real time; signal generator and detector (e.g., X-ray generator and detector); a processor for measuring an electric field, an impedance, and a current generated from the electromagnetic actuation system; a high-voltage system for the signal generator; a cooling system; a location recognizing device for grasping the location of the microrobot; or a controller for commanding the current control of the 3-axis Helmholtz coils so as to control the track of the microrobot, on the basis of the microrobot motion information detected by the location recognizing device and the microrobot route information that has been previously input.

III. Medical Microrobot System

In accordance with still another aspect of the present invention, there is provided a medical microrobot system including:
(a) a microrobot main body 100 including a helical head 110, a rotatable spherical joint 120, and a magnetic substance 130;
(b) an electromagnetic navigation system (ENS) 200; and
(c) a three-dimensional imaging system 300.

The present inventors implemented an improved electromagnetic navigation system (ENS), which uses a high-frequency operation based on a resonant effect, in order to enhance the drilling force of the microrobot.

A microrobot system of the present invention is a medical robot system utilizing the helical microrobot and the electromagnetic navigation system.

The present inventors verified through in-vitro experiment results that the electromagnetic navigation system successfully enhanced the locomotive force and drilling force of the microrobot and thus can be applied for mechanical thrombectomy in cardiovascular therapeutics.

The medical microrobot system of the present invention was designed to alleviate occlusion, that is, an obstructive disease in which a blood vessel or a tube constituting a lumen is blocked.

Examples of the obstructive disease may include thrombosis, embolism, thromboangiitis obliterans, obstructive and constrictive cerebrovascular diseases, obstructive and constrictive cardiovascular diseases, peripheral vascular obstructive diseases, and atherosclerosis, but are not limited thereto.

Thrombosis is a disease in which blood clots are formed to prevent the flow of blood in the blood vessel.

Embolism is a disease in which a material from the circulating system blocks the blood vessel. Embolism refers to the simultaneous accompanying thrombosis and embolism.

Thromboangiitis obliterans or Buerger's disease is a vascular disease that causes the blockage of arterial flow due to an inflammation in small and medium arteries with a relatively small diameter and results from the obstruction of blood vessels.

Examples of obstructive and constrictive cerebrovascular diseases include cerebral infarction, stroke, or moyamoya disease.

Examples of obstructive and constrictive cardiovascular diseases include angina, myocardial infarction, or the like.

Peripheral vascular obstructive diseases are diseases that are mainly caused by narrowing of a blood vessel due to atherosclerosis, and may damage the functions of organs receiving blood flows from the corresponding blood vessel, resulting in amputation and even death.

The peripheral blood vessels mean arteries and veins diverging from the aorta and the vena cava, and lymphatic vessels.

Atherosclerosis is a vascular disease in which atheroma is formed, and this disease is mainly caused by the deposition of cholesterol on the endothelium covering the innermost side of the blood vessel and the proliferation of endothelial cells. The inside of the atheroma thins out like porridge and the surrounding area thereof is surrounded by a hard fibrous membrane, a plaque. The unstable plaque ruptures to generate a thrombus in the blood vessel.

The vascular obstruction has been mainly treated using a catheter until now. However, when the blood vessel is completely occluded by thrombi (e.g., chronic total occlusion (CTO)), a guidewire inducing the catheter is difficult to insert.

In order to overcome such difficulty in catheterization, a system has been developed capable of tunneling a completely occluded area through drilling or hammering by operating a microrobot inserted into the blood vessel, remotely from the outside of the body.

Hereinafter, the medical microrobot system of the present invention will be described in detail.

1. Guide-Wired Helical Microrobot—Microrobot Main Body 100

The helical microrobot of the present invention was designed such that the helical microrobot can effectively perform drilling, steering, and propulsion functions against strong blood flow in blood vessels.

The microrobot of the present invention includes a helical head for performing drilling and rotating motions. The helical head is rotated using an external rotary magnetic field by an electromagnetic navigation system (ENS).

The microrobot main body of the present invention may be equipped with a rotatable spherical joint or ball joint in the tip thereof. Alternatively, the microrobot main body of the present invention may be equipped with a revolute joint (one degree of freedom) in the tip thereof.

The spherical joint or revolute joint may be connected to a guidewire. According to an embodiment of the present invention, the guidewire is a magnetically steering guidewire that is controlled by the electromagnetic navigation system (ENS). The guidewire may be connected to and controlled by a guidewire feeder.

Since the microrobot is very small, a battery or a controller cannot be inserted into the microrobot. In order to overcome such a disadvantage, the microrobot is actuated by the force of an electromagnetic field by using an external electromagnetic coil system. According to an embodiment of the present invention, a magnetic substance is installed inside the microrobot to perform the deriving of the robot by electromagnetic force. The magnetic substance may be a paramagnetic substance or a ferromagnetic substance. For example, the magnetic substance may be a permanent magnet or an electromagnet. The electromagnet can perform the switch of magnetization orientation and the ON/OFF of magnetization.

The magnetization orientation of the magnetic substance may be appropriately set considering the direction of an external electromagnetic field. According to an embodiment of the present invention, the magnetization orientation of the magnetic substance is orthogonal to the axis of the microrobot main body. The magnetic substance inside the microrobot can be aligned in a direction of a magnetic field by an externally applied magnetic field so as to match the magnetization orientation.

The microrobot of the present invention can perform a rotation motion, a translation motion, or a drilling motion (or hammering motion) in the blood vessel. The microrobot of the present invention can perform the rotation motion, the translation motion, or the drilling motion at different times or at the same time. For example, during locomotion (or a translation motion) of the microrobot, the microrobot can perform a rotation or drilling motion together.

2. Electromagnetic Navigation System (ENS)

For actuation and control of the microrobot, proposed in the present invention is an electromagnetic navigation system employing: (i) a resonant control circuit; and (ii) an automatic pseudo-continuous capacitance switching method capable of maintaining a high current in a wide range of operating frequency.

This system naturally switches the capacitance to enable the continuous frequency shift to a desired frequency. The in-vitro experiment results in the examples of the present invention show the feasibility of a mechanical thrombectomy system for clinical application in practice.

As used herein, the term "electromagnetic navigation system (ENS)" refers to a system that performs the integrative control of the microrobot and the electromagnetic actuation system. The electromagnetic navigation system can control the actuation of the microrobot by generating a high frequency and an electromagnetic field. The magnetic substance inside the microrobot interacts with the electromagnetic field generated by the electromagnetic navigation system to control the motions of the microrobot.

Herein, the electromagnetic navigation system includes an electromagnetic actuation (EMA) system that controls the three-dimensional locomotion and directions of the helical microrobot.

In addition, the electromagnetic navigation system may include: a monitor for observing the microrobot in real time; signal generator and detector (e.g., X-ray generator and detector); a processor for measuring an electric field, an impedance, and a current generated from the electromagnetic actuation system; a high-voltage system for the signal generator; or a cooling system.

Therefore, an operator (e.g., a surgeon) can track or determine the location of the microrobot in a three-dimensional space by using the electromagnetic navigation system.

As used herein, the term "electromagnetic actuation (EMA) system" refers to a system that controls the three-dimensional locomotion and direction of a microrobot. The electromagnetic actuation system of the present invention includes a resonance control circuit, and can generate a wide range of resonant frequency with a maximum magnetic field and little phase delay. FIG. 5 shows a wide operating frequency range of the ENS of the present invention. The controllable lowest to highest resonant frequencies of CHCx, SHCy, and SHCz shown in FIG. 5 are 16.58-100 Hz, 26.27-131.2 Hz, and 41.42-370 Hz, respectively. The operating frequencies of ENS can be controlled by an operator depending on the degree of blood vessel calcification, and thus can change the cutting rotation torque.

The electromagnetic actuation system includes a magnetic field generator that generates a magnetic field in any detection on three dimensions.

The magnetic field generator is configured to generate a magnetic field so as to rotate the helical microrobot or allow the microrobot to perform a translation motion in any direction, and includes a uniform magnet field generation module and a gradient magnet field generation module.

The uniform magnetic field generation module generates a uniform magnetic field, which produces the torque to align the microrobot in a three-dimensional space to thereby align the microrobot in any direction and changes the alignment direction of the microrobot so as to enable the rotational motion of the microrobot. The gradient magnet filed generation module generates a gradient magnetic field to allow the microrobot to perform a propulsion motion in a predetermined direction.

The magnetic field generator may be composed of a combination of various coils that generate a constant magnetic flux through magnetization currents. For example, the magnetic field generator may include Maxwell coils, Helmholtz coils, saddle coils, or a combination thereof. The magnetic field generator can generate a magnetic field in any direction on three dimensions by adjusting the intensity and orientation of the magnetization current in each coil.

According to an embodiment of the present invention, the electromagnetic actuation system includes three pairs of air-core type electromagnetic coils (i.e., 3-axis Helmholtz coils) orthogonal to each other, wherein the variable capacitor circuit is connected to each coil in series to form an electromagnetic actuator (EMA) circuit.

According to a particular embodiment of the present invention, circular Helmholtz coils and square Helmholtz coils may be used in the electromagnetic actuation system. Especially, the electromagnetic actuation system may be designed such that two pairs of square Helmholtz coils are placed inside the circular Helmholtz coils to maximize the region of interest (ROI).

According to an embodiment of the present invention, the electromagnetic actuation system includes a resonance control circuit in which two pairs of square Helmholtz coils are placed inside one pair of circular Helmholtz coils. A magnetic field necessary for actuation may be generated according to the current value applied to each coil.

According to an embodiment of the present invention, the microrobot of the present invention is externally controlled by the electromagnetic actuation (EMA) system.

The external control means that a device (microrobot) is controlled by an operator outside an operating room so that the operator can avoid the exposure to X-ray or an electromagnetic field.

The microrobot of the present invention is actuated by the force of the electromagnetic field generated from the electromagnetic coils of the electromagnetic actuation system. That is, the microrobot of the present invention is actuated by an interaction between the electromagnetic field generated from external electromagnetic coils and the magnetic substance inside the microrobot.

3. Three-Dimensional Imaging System

To real-time monitor the above-described helical microrobot, a three-dimensional imaging system is used.

The three-dimensional imaging system of the present invention may include X-ray fluoroscopy, computed tomography (CT), positron emission tomography (PET), positron emission tomography-computed tomography (PET/CT), radioisotope imaging (RI), or ultrasonography.

Examples of the X-ray fluoroscopy include mono-plane X-ray fluoroscopy, bi-plane X-ray fluoroscopy, or multi-plane X-ray fluoroscopy.

According to an embodiment of the present invention, the imaging system is bi-plane X-ray fluoroscopy.

According to another embodiment of the present invention, the imaging system may be configured of: an X-ray fluoroscopy module for obtaining images of the microrobot; and an image merging module that merges the images obtained from the X-ray fluoroscopy module with previously photographed images of a subject to track and display the location of the microrobot.

According to an embodiment of the present invention, the medical microrobot system of the present invention may further include a suction device. For example, the helical microrobot and the suction device of the present invention may be inserted through a catheter (see FIG. 7), and the thrombus broken by the helical microrobot is collected through the suction device and discharged to the outside.

According to an embodiment of the present invention, the medical microrobot system of the present invention may further include a location recognizing device for grasping the location of the microrobot.

According to another embodiment of the present invention, the medical microrobot system of the present invention may further include a controller that commands the current control of the 3-axis Helmholtz coils to control the track of the microrobot, on the basis of the microrobot motion information detected by the location recognizing device and the microrobot route information that has been previously input.

Advantageous Effects

The present invention is directed to a novel guide-wired helical microrobot for mechanical thrombectomy applied to a calcified thrombus and, specifically, to an electromagnetic navigation system (ENS) using the high-frequency operation based on a resonant effect to enhance the drilling force of the microrobot. The microrobot system of the present invention can accurately tunnel a vascular occlusion area without damaging vascular walls through an electromagnetic navigation system, and shortens the recovery period after surgery through the minimization of an invasive area, leading to an improvement in life quality of a patient. Furthermore, the electromagnetic navigation system of the present invention enables remote steering outside a surgery room, therefore causing no risk of an operator exposing to radiation. The microrobot system of the present invention has a wide range of application, such as thrombosis, thromboangiitis obliterans caused by vascular occlusion, cerebral infarction, stroke, angina or myocardial infarction, peripheral vascular obstructive diseases, or atherosclerosis.

BRIEF DESCRIPTION OF THE DRAWINGS

R: Radius of microrobot body
2r: Helical thickness
λ: Helical pitch
T: Rotation period, w: angular speed
F: propulsion force, u: speed

α: angle between x-y plane and magnet, θ: angle between x-axis and magnet
u: vector of projection direction (heading direction) of microrobot, n: vector of rotational direction

DETAILED DESCRIPTION

Hereinafter, the present invention will be described in more detail with reference to examples. These examples are only for illustrating the present disclosure more specifically, and it would be apparent to those skilled in the art that the scope of the present disclosure is not limited by these examples according to the gist of the present disclosure.

Examples

I. Present Inventive System Overview

Figure 1:
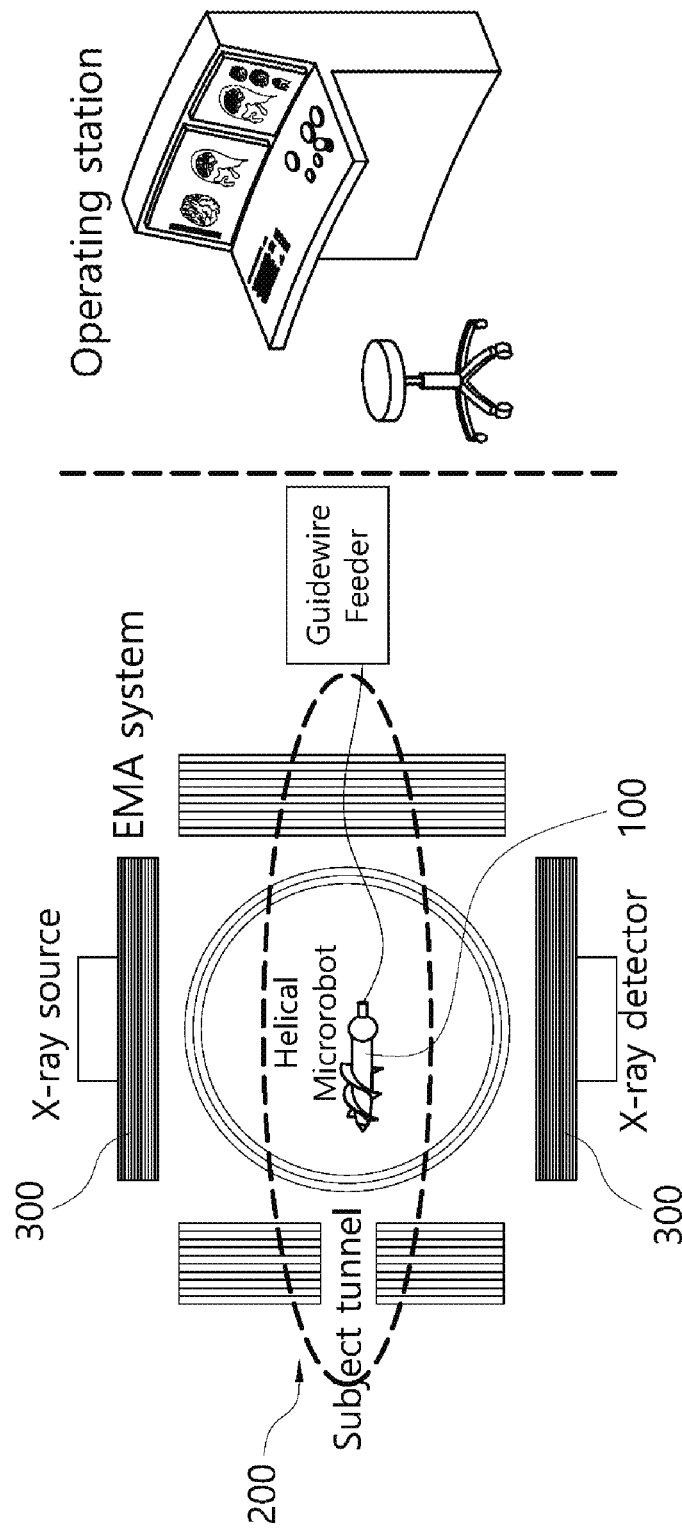
FIG. 1 shows the entire structure of a guide-wired helical microrobot system of the present invention.

From the point of view of a practical fully controllable helical microrobot, the system of the present invention is at least composed of a helical microrobot, an electromagnetic navigation system (ENS), and an imaging system (see FIG. 1).

The microrobot is externally controlled by an electromagnetic actuation (EMA) system in the ENS. This microrobot is controlled outside an operating room so that an operator can avoid X-ray exposure. The key components of the medical microrobot system of the present invention are as follows.

A. Helical Microrobot for Intravascular Drilling

For the effective locomotion and drilling of the microrobot in the blood vessel, the microrobot needs to be helical or spiral. The size of the robot needs to be minimized for the insertion into the blood vessel and the improvement of locomotion.

In order to externally actuate the microrobot by using the electromagnetic navigation system (ENS) that provides sufficient force to implement external actuation and drilling motion, a small-sized permanent magnet is placed inside the robot main body.

The magnetization direction of the microrobot is also important capable of designing control strategies of ENS.

B. Electromagnetic Navigation System (ENS) for External Actuation

ENS plays an important role to generate a magnetic field necessary for producing the torque to align the microrobot and the force to control and actuate the microrobot in a three-dimensional space by utilizing a uniform magnet field and a gradient magnet field.

In previous studies, the present inventors successfully demonstrated several configurations and sizes of ENS based on air-core type electromagnets that enables the 3D locomotion of the microrobot.

C. Imaging System for Microrobot Tracking

Tracking and recognizing the direction and location of the robot in the human body is an important issue in clinical applications. This is associated with targeting accuracy and intravascular intervention safety and further a remote control application of a microrobot during the mechanical thrombectomy procedure. Since X-ray fluoroscopy is currently available in the operating room, an X-ray imaging system was used in the present invention.

As an alternative, an MRI system can be used to simultaneously manipulate and recognize an object. However, the control sequencing for monitoring conflicts with the control, and thus a relatively small actuation force has been generated in actuation of the microrobot in the blood vessel.

Figure 2A:
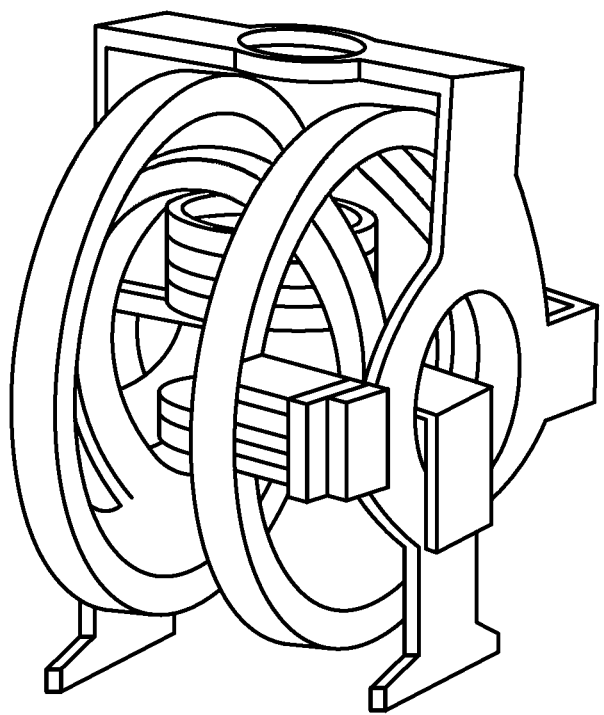
FIG. 2A shows an ENS system used in the present invention.
Figure 2B:
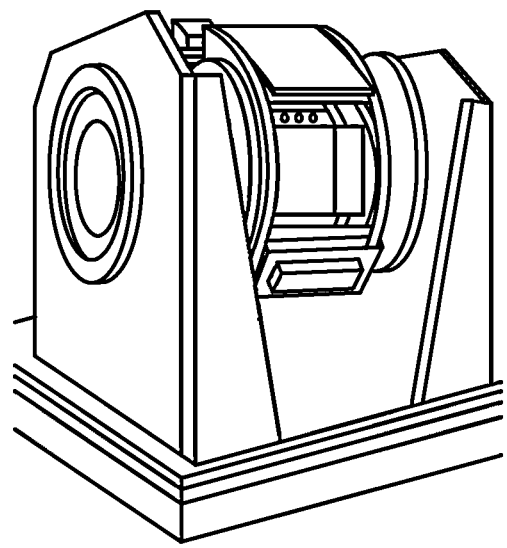
FIG. 2B shows an ENS platform of the present invention using bi-plane X-ray fluoroscopy.
Figure 2C:
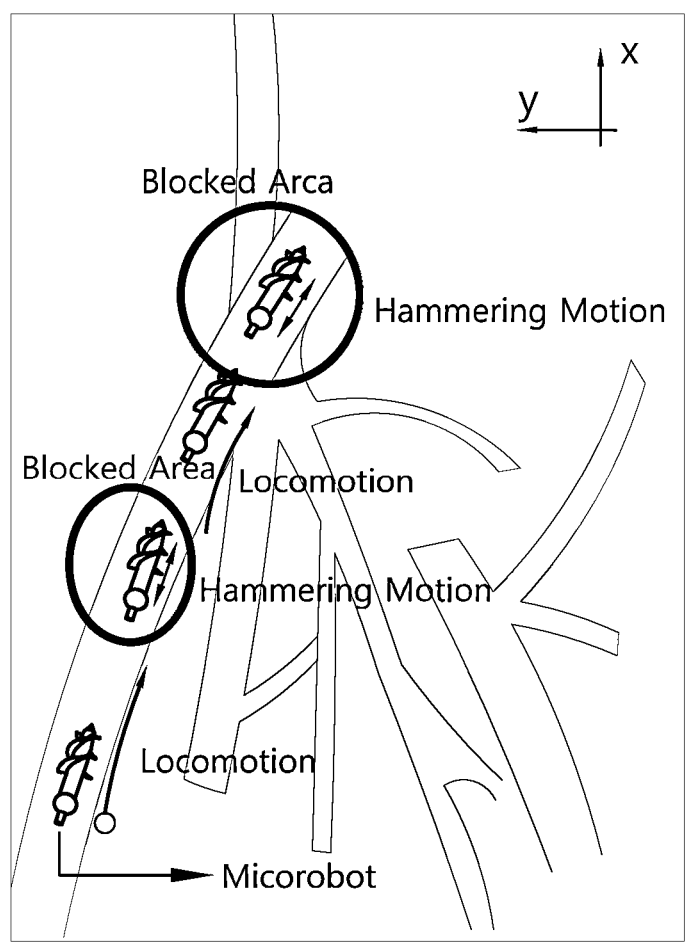
FIG. 2C shows a tracking image of the helical microrobot of the present invention in the blood vessel.

Hence, the imaging system of the present invention has been developed to have capability of grasping and detecting the location of the microrobot by utilizing bi-plane X-ray fluoroscopy through three dimensional object reconstructions (see FIGS. 2B and 2C).

II. Improved Helical Microrobot System

Hereinafter, a mechanical thrombectomy device of the present invention will be described. More specifically, the structure of a guide-wired helical microrobot and a power- and frequency-range improved ENS will be described.

A. Guide-Wired Helical Microrobot

Figure 3A:
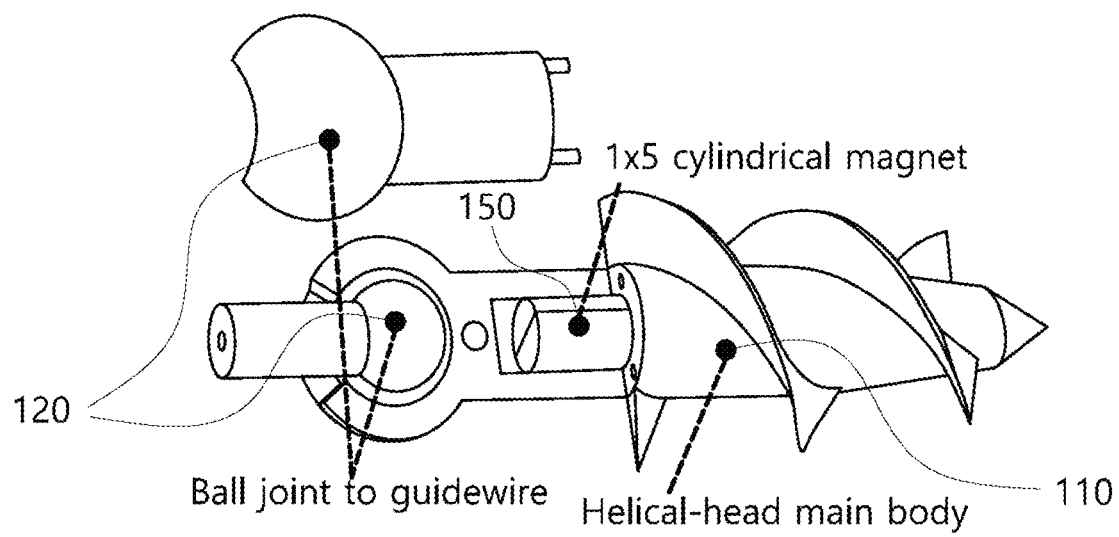
FIG. 3A shows a structural design of a microrobot.
Figure 3B:
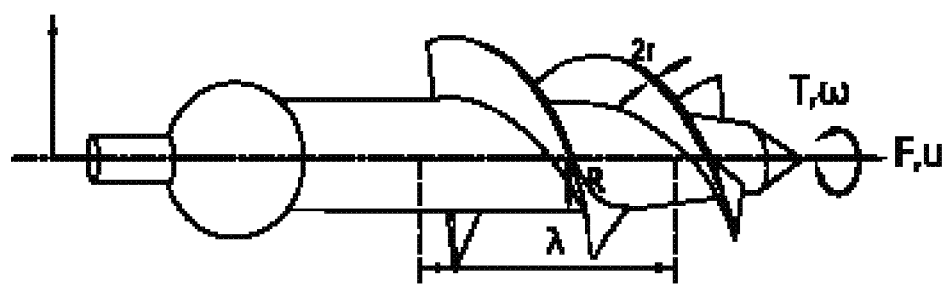
FIG. 3B shows a 3D-printed helical robot. The F-directional arrow represents the X-directional coordinate system of the microrobot. The arrow at the tip of the microrobot represents the Y-directional coordinate system.
Figure 3C:
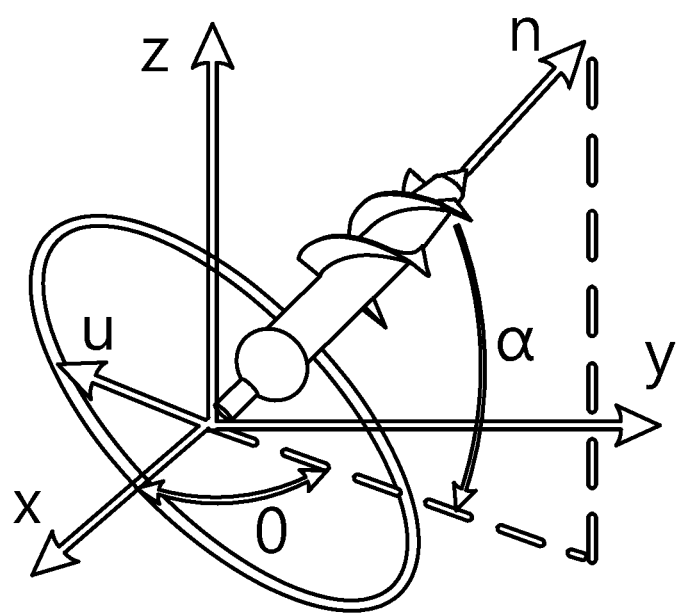
FIG. 3C shows the locomotion coordinate of a helical microrobot having a predetermined rotating electromagnetic field.

FIG. 3A shows a structure of a helical microrobot, and FIG. 3B shows a prototype of the helical microrobot, made by a 3D printer (VeroClear-RGD810 from Stratasys).

The device of the present invention is equipped with a rotatable spherical joint in the tip of the helical microrobot, and the spherical joint is connected to a guidewire.

The guidewire connection is performed for the purpose of supporting the microrobot against the blood flow in the blood vessel.

Moreover, the spherical joint enables the supporting guidewire to maintain the drilling motion without twisting. The geometric parameters of the helical-head guidewire are summarized in Table 1.

TABLE 1

| Parameter | Explanation | Value |
| --- | --- | --- |
| R | Body radius [mm] | 1 |
| λ | Helix pitch [mm] | 5.5 |
| 2r | Spiral thickness [μm] | 120 |
| — | Spiral height [mm] | 1.2 |
| — | Head length [mm] | 12 |
| — | Permanent magnet [mm] | 1 (diameter) × 5 (length) |

The main body size of the microrobot was minimized so that the microrobot was inserted into a commercially available catheter for artery therapeutics. A permanent magnet is placed inside the main body in order to interact with the electromagnetic field generated by ENS to control the motion. The magnetization orientation of the tip is orthogonal to the axis of the main body. The ball joint is designed such that a 0.011" super-elastic guidewire is connected to the microrobot main body. The length and forward and backward motions of the guidewire is controlled by a guidewire feeder.

B. Power- and Frequency-Range Improved ENS

Three orthogonal pairs of air-core type electromagnetic coils are used in ENS:
circular Helmholtz coils (CHCx); and
y- and z-directional square Helmholtz coils, SHCy and SHCz, respectively.

Figure 4A:
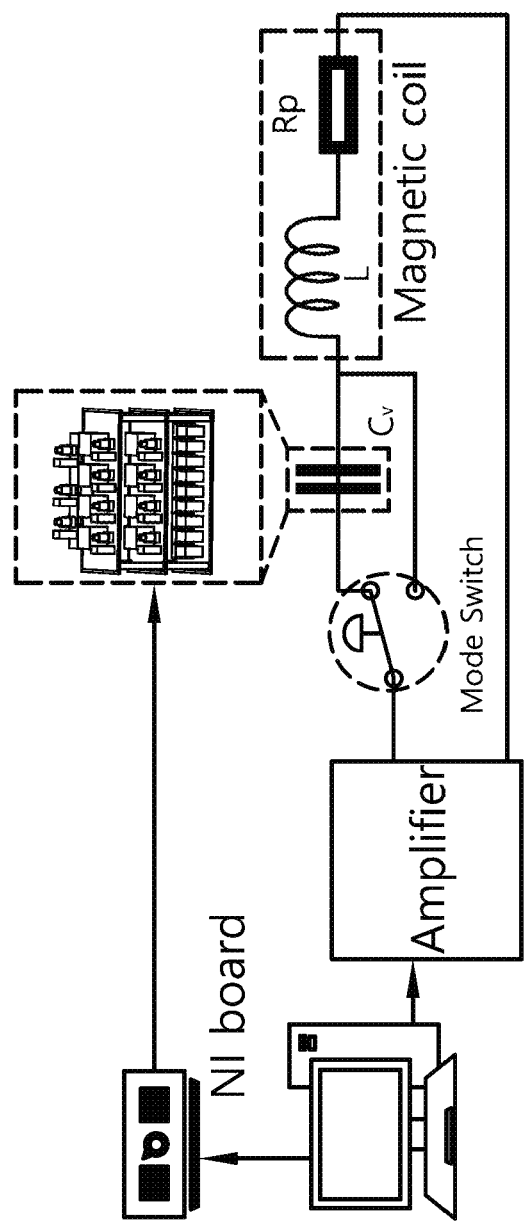
FIG. 4A shows a conceptual design of an electromagnetic actuator circuit applying a resonance control system. Rp: Internal resistance
Figure 4B:
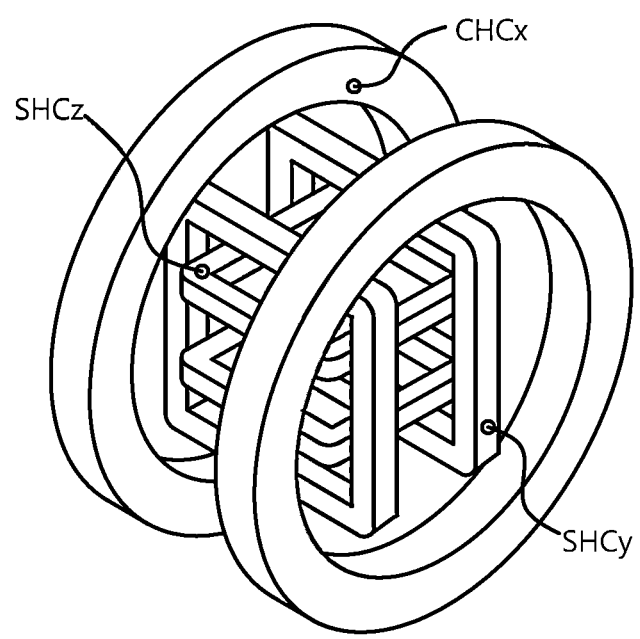
FIG. 4B shows one embodiment of an electromagnetic coil contained in an electromagnetic actuator circuit of the present invention. CHCx: x-directional circular Helmholtz coil, SHCy: y-directional square Helmholtz coil, SHCz: z-directional square Helmholtz coil.

Two pairs of square Helmholtz coils were designed inside the circular Helmholtz coils to maximize the region of interest (ROI) (see FIG. 4B). The frame of this system was designed to adopt a nonconductive material (Bakelite) to avoid eddy current effects and heat emission.

The detailed specifications of ENS are shown in Table 2.

TABLE 2

| Specification | CHCx | SHCy | SHCz |
| --- | --- | --- | --- |
| Coil radius/length (mm) | 162 | 168 | 120 |
| Number of turns | 472 | 380 | 300 |
| Resistance (Ohm) | 6.75 | 9.27 | 5.42 |
| Inductance (mH) | 258 | 92 | 37 |
| Magnetic field intensity (A/m) | 1982.4 | 2679.1 | 2913.3 |

Since the electromagnetic coils are made by copper coil winding, the magnetic flux density reduction and phase delay are unavoidable due to an inductance effect. In the three pairs of coils, the magnetic flux density dramatically decreased and the phase delay increased with respect to the operating frequency. In experiments, the magnetic flux density showed a reduction of 90% and the phase delay showed an increase of 90° with respect to a frequency variation of approximately 30-300 Hz.

Therefore, to enhance the actuation force and widen the operating frequency range of the ENS system, the inductance effect needs to be reduced. An inductance reduction circuit and a pseudo-continuous switching algorithm were designed using a variable capacitor circuit composed of various capacitors, relays, and switching circuits, in each coil. Assuming that each coil is a simple RL circuit, the variable capacitor circuit to each coil in series forms an RLC equivalent circuit as shown in FIG. 4A. Then, the output current (I(s)) of the RLC circuit is calculated as followings $$I(s) = \frac{sC_v V_i(s)}{LC_v s^2 + RC_v s + 1} \quad (1)$$

s: Laplace constant
Cv: Variable capacitance value
Vi: Input voltage
L: Coil inductance
R: Resistance value in RLC circuit The phase of the RLC circuit is as follows:

$$\phi = \tan^{-1}\left(\frac{2\pi fL}{R} - \frac{1}{2\pi fRC_v}\right) \quad (2)$$

where Cv was designed as a variable capacitor that can match the resonant frequency of the coil system. For the given desired frequency, the capacitor is automatically switched to match the coil impedance and then cancel the inductor reactance by changing the capacitance.

The circuit will resonate at the following frequency:

$$f_r = \frac{1}{2\pi\sqrt{LC_v}} \quad (3)$$

$V_L = 2\pi fLI_0$, $V_C = I_0/(2\pi fC_v)$, and $C_v = 1/(2\pi f)^2 L$ were set. Therefore, the voltages at both ends of the coil and the capacitor were equal $V_L = V_C$, and the net voltage across the coil and the resonance control circuit became 0 V by the Kirchhoff's voltage law. Since the remaining parasitic resistance was relatively small, the applied voltage to maintain the parasitic resistance can deliver the maximum current with a zero phase delay through the ENS at the given input frequency.

III. Results

Figure 5:
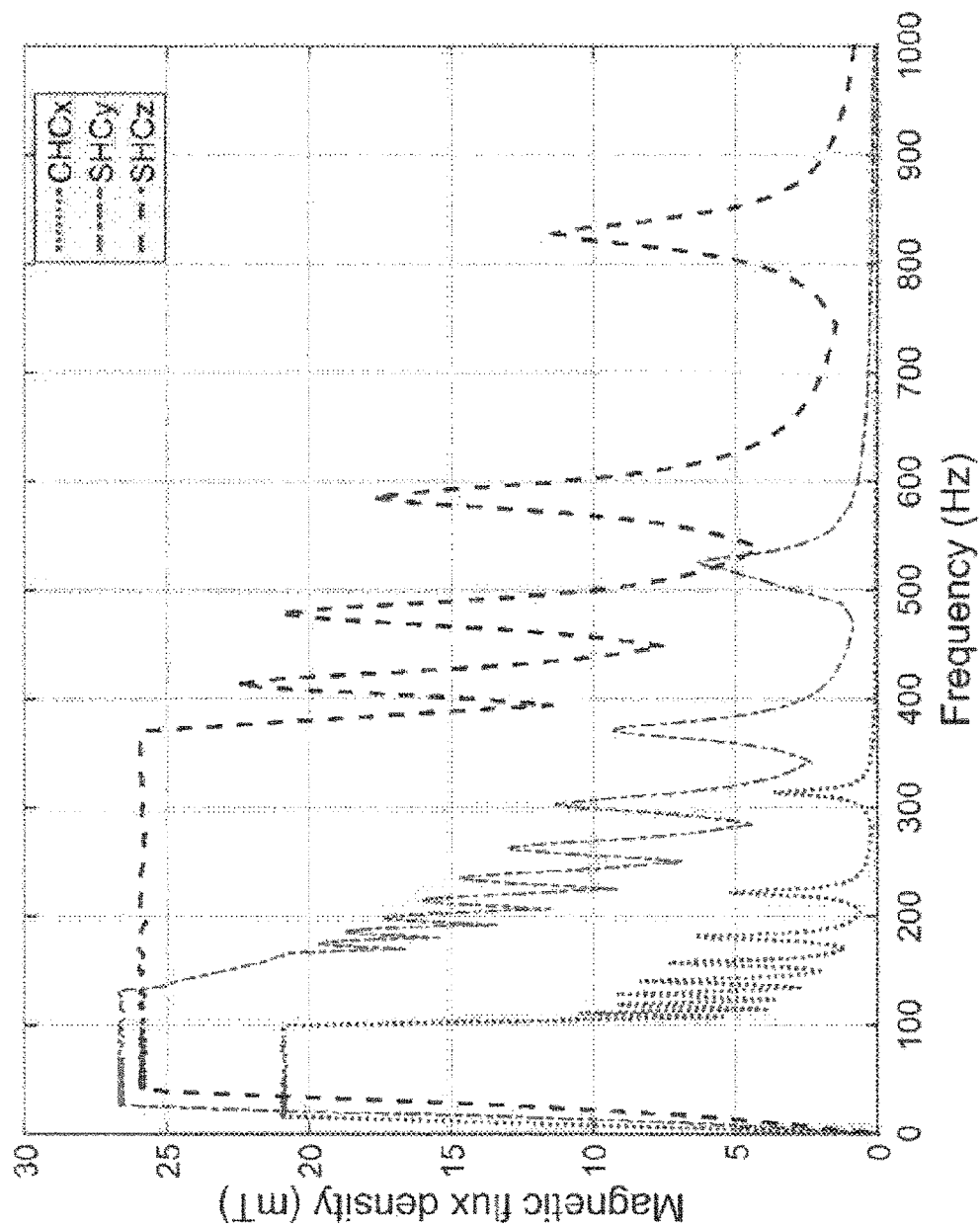
FIG. 5 shows the maximum magnetic flux density and available operating frequency range of the ENS system of the present invention with a series resonance control system.

FIG. 5 shows the wide operating frequency range of the ENS of the present invention. The controllable lowest to highest resonant frequency ranges of CHCx, SHCy, and SHCz were 16.58-100 Hz, 26.27-131.2 Hz, and 41.42-370 Hz, respectively. The CHCx coil had a lowest maximum operating frequency of 100 Hz. The coil system requires a high voltage to maintain a high coil current, and the reason is that the coil system shows the largest inductance value, resulting therefrom.

To examine the resonance control circuit suggested in the present invention, the step-out frequency experiment was performed. The step-out frequency is directly related to the actuation force of the microrobot. The rotating magnetic field frequency was continuously increased until the microrobot speed dropped down, and the input frequency was regarded as the limit frequency of the microrobot motion. As a result, the step-out frequency of a robot without a resonance control system was around 50 Hz, but the step-out frequency of the ENS of the present invention showed 200 Hz, which was much higher than that of the previous system. Since the step-out frequency could be improved by 400%, the locomotion speed was improved by approximately 388% (As the input frequency increases, the varying speed of the magnetic field, and thus the rotating speed of the robot increases, resulting in an increase in locomotion speed of the microrobot).

Figure 6A:
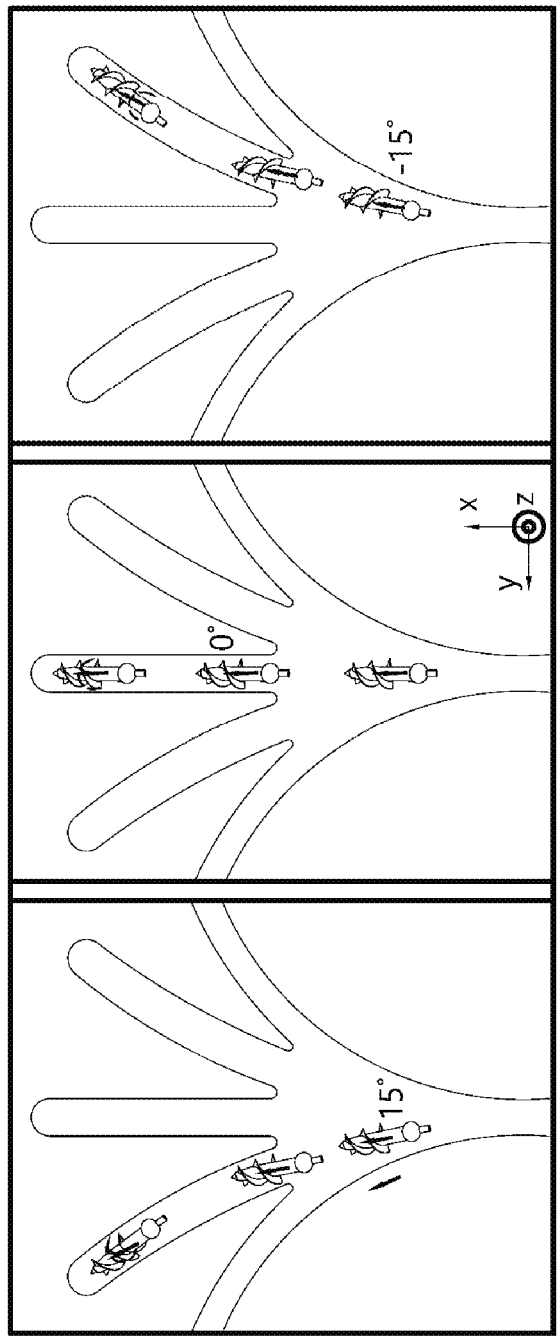
FIG. 6A shows in-vitro experimental results of a guide-wired microrobot, depicting the locomotion and drilling motions in a 5-branch phantom (4 mm in diameter).
Figure 6B:
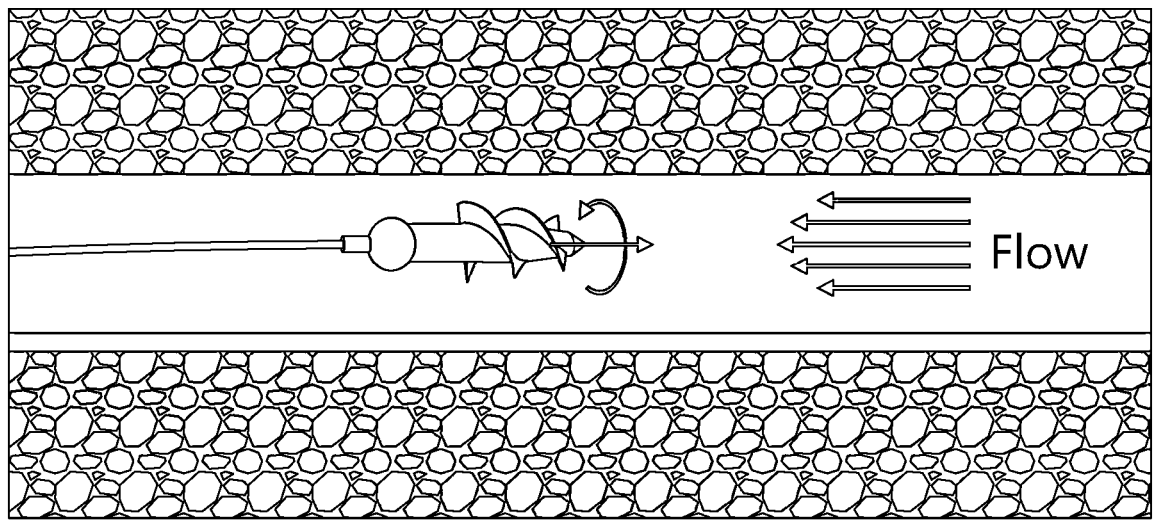
FIG. 6B shows in-vitro experimental results of a guide-wired microrobot, depicting the actuation and drilling motion in a flow tube.
Figure 7:
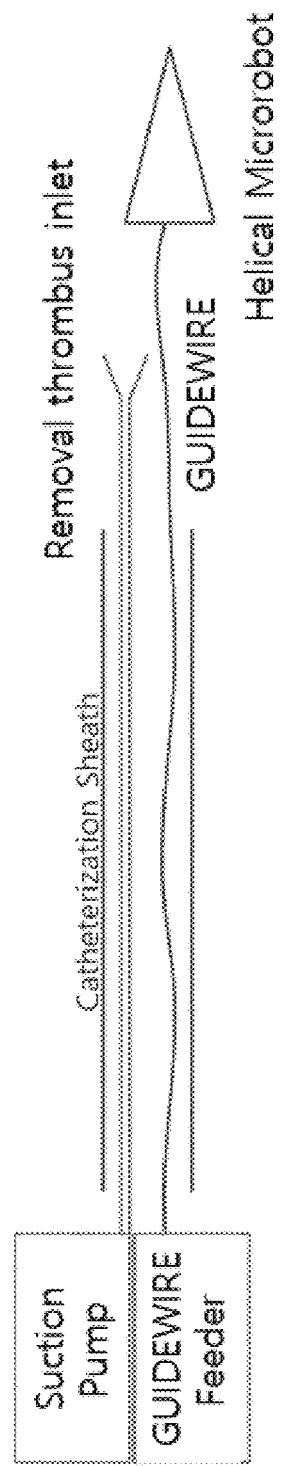
FIG. 7 schematically shows a guide-wired microrobot and a suction device of the present invention, which are inserted through a catheter.

To show the feasibility of the guide-wired helical microrobot system of the present invention, two in-vitro experiments were conducted: direction control into different branches (FIG. 6A) and driving force and drilling force in the water flowing tube (FIG. 6B).

As shown in FIG. 6A, the three-dimensional control force and the obstacle removal motion experiments of the helical microrobot were conducted in the phantom with five branches.

First, the guide-wired microrobot was controlled to move into different directions of the phantom branches of 15°, 0°, and −15°.

Second, after successful guidewire was inserted into a desired branch, the drilling motion and propulsion were performed simultaneously for the effective removal of an obstacle. For the application of mechanical thrombectomy, a 3D printed phantom was made to mimic the blood vessel environment. To mimic an obstacle in the human blood vessel, an agar-block region (0.5% agarose which was 7 times harder than a previous one [F. Carpi et al., IEEE Trans. Biomed. Eng., vol. 58, no. 2, pp. 231-234, 2011]) was made at the end of the desired portion.

The system of the present invention could effectively drill through the obstacle within 20 seconds, indicating a significant increase in drilling force (see FIG. 6A).

The effect of the guidewire method against flow was evaluated in the water flow tube as shown in FIG. 6B. The guide-wired microrobot could maintain its position during drilling motion and move forward and backward freely without being influenced by the water flow. Furthermore, the guide-wired microrobot could move forward and backward while simultaneously performing drilling motion.

IV. Conclusion

The present invention verified the feasibility of the novel mechanical thrombectomy device using the guide-wired helical microrobot and the improved ENS system. A prototype of the helical microrobot having a spherical joint connected to the guidewire was constructed, and the drilling motion and steering locomotion of the microrobot were verified through in-vitro experiments. Furthermore, a resonance control system generating a high frequency and an electromagnetic field was developed to enhance drilling force of the helical microrobot system of the present invention.

It was experimentally proved that the ENS of the present invention could generate a wide range of resonant frequency with a maximum magnetic field and little phase delay. Furthermore, the motional controllability and drilling forces could be obtained to remove a thrombus in the vascular system.

INDUSTRIAL APPLICABILITY

The present invention relates to a guide-wired microrobot system for mechanical thrombectomy. More specifically, the present invention relates to a medical robot system composed of a helical microrobot equipped with a guidewire at the tip thereof, an electromagnetic actuation system for rapidly rotating the helical microrobot, and a real-time imaging system.

What is claimed is:

1. A medical microrobot system comprising:
    (a) a microrobot main body comprising a helical head, a rotatable spherical joint, and a magnetic substance;
    (b) an electromagnetic navigation system (ENS); and
    (c) a three-dimensional imaging system
        wherein the electromagnetic navigation system comprises an electromagnetic actuation (EMA) system for controlling the microrobot main body,
        wherein the electromagnetic actuation system comprises 3-axis Helmholtz coils and variable capacitors, and
        wherein the 3-axis Helmholtz coils comprise one pair of circular Helmholtz coils disposed in an x-axial space, a first pair of square Helmholtz coils disposed in a y-axial space, and a second pair of square Helmholtz coils disposed in a z-axial space.

2. The medical microrobot system of claim 1, wherein the rotatable spherical joint is installed in a tip of the microrobot main body and the spherical joint is connected to a guidewire.

3. The medical microrobot system of claim 1, wherein the guidewire is a magnetically steering guidewire.

4. The medical microrobot system of claim 1, wherein the variable capacitors are connected in series to the 3-axis Helmholtz coils, respectively, to form a resonance control circuit.

5. The medical microrobot system of claim 1, wherein the imaging system comprises X-ray fluoroscopy, computed tomography (CT), positron emission tomography (PET), positron emission tomography-computed tomography (PET/CT), radioisotope imaging (RI), or ultrasonography.

6. The medical microrobot system of claim 5, wherein the X-ray fluoroscopy is mono-plane X-ray fluoroscopy, bi-plane X-ray fluoroscopy, or multi-plane X-ray fluoroscopy.

7. The medical microrobot system of claim 1, wherein the magnetic substance is a permanent magnet or an electromagnet.

8. The medical microrobot system of claim 1, further comprising a suction device.

* * * * *